United States Patent [19]

Marshall

[11] Patent Number: 5,310,502
[45] Date of Patent: May 10, 1994

[54] HIGH TILT ANGLE FLC MIXTURE FOR TIR SWITCHING DEVICES

[75] Inventor: Kenneth L. Marshall, Henrietta, N.Y.

[73] Assignee: The United States of America as represented by the Secretary of the Air Force, Washington, D.C.

[21] Appl. No.: 722,022

[22] Filed: Jun. 27, 1991

[51] Int. Cl.$^5$ .................. C09K 19/12; C07C 69/76
[52] U.S. Cl. .................. 252/299.65; 560/73
[58] Field of Search .................. 252/299.01, 299.65; 359/104; 560/73

[56] References Cited

U.S. PATENT DOCUMENTS

| | | | |
|---|---|---|---|
| 4,834,907 | 5/1989 | Inoue et al. | 252/299.65 |
| 4,966,727 | 10/1990 | Ichihashi et al. | 252/299.65 |
| 5,076,962 | 12/1991 | Furukawa et al. | 252/299.65 |
| 5,114,614 | 5/1992 | Emoto et al. | 252/299.65 |

FOREIGN PATENT DOCUMENTS 3151349 6/1991 Japan .

Primary Examiner—Philip Tucker
Attorney, Agent, or Firm—Donald J. Singer; Thomas C. Stover

[57] ABSTRACT

The invention provides a series of ferroelectic smectic liquid crystal compounds, FLC, of wide tilt angle and mixtures formulated from them that are useful for high speed modulation or switching of optical radiation. Such FLC mixtures are useful in total internal reflection, TIR switching devices. In such TIR switches, an applied DC voltage rotates the molecules through about a 90° angle which changes the perceived refractive index at the FLC layer and permits rapid optical switching. For an FLC crystal material to be useful in such a device it must possess a value of molecular tilt angle $\theta$ of approximately 45°, since the dipole molecule rotates through an angle of about 2 $\theta$ upon application of a DC field to the cell. This requirement for a large molecular tilt angle greatly limits the compounds and mixtures thereof which can be employed in such TIR devices.

The smectic FLC compounds and mixtures thereof of the present invention provide for TIR switches that exhibit high contrast ratios ( <1,000:1). They can also provide in such switch, 2-position bistable beam deflection. That is, if the electric field of the TIR switches is shut off, the smectic FLC compounds will hold the molecular tilt angle existing at that time without requiring an applied electric field (to hold such pattern) unlike their nematic LC predecessors.

1 Claim, 3 Drawing Sheets

HIGH TILT ANGLE FLC MIXTURE FOR TIR SWITCHING DEVICES

STATEMENT OF GOVERNMENT INTEREST

The invention described herein may be manufactured and used by or for the Government for governmental purposes without the payment of any royalty thereon.

BACKGROUND OF THE INVENTION

1. Field of the Invention

This invention relates to high tilt angle FLC mixtures for TIR switching devices, particularly the high tilt angle compound employed in such mixtures.

2. The Prior Art

Ferroelectric liquid crystals (FLC's) are well known for their ability to switch optical radiation in the the microsecond regime as opposed to conventional nematic liquid crystals, whose response times are generally limited to tens of milliseconds. Schematic diagrams of a typical surface stabilized ferroelectric liquid crystal cell, as first proposed by Clark and Lagerwall are shown in FIGS. 1 and 2; See N. A. Clark and S. T. Lagerwall, "A Microsecond-Speed, Bistable, Threshold-Sensitive Device", in Liquid Crystals of One-and Two-Dimensional Order, W. Helfrich and G. Heppke, Eds, Springer-Verlag, New York, 22 (1980), incorporated herein by reference. The layer planes of the smectic structure are normal to the cell substrates, while the smectic molecules lie parallel to the substrates and make an angle with the layer planes, which is defined as the tilt angle $\theta$. Application of a DC electric field causes the molecules to reorient through an angle which is approximately equal to $2\theta$. The value of $\theta$ is determined by the molecular structure of the smectic liquid crystal molecule and for most materials is typically 19°–23°. If a device containing such a material be placed between crossed polarizers and aligned so that the initial molecular orientation is parallel to one of the polarizers (non-transmissive state), an electric field causes the molecules to rotate through an angle of approximately 45° and the device behaves like a uniaxial wave plate ($\Delta n = n_e - n_o$, transmissive state). Since this type of device configuration is the most commonly employed, numerous liquid crystal mixtures with small tilt angles (19°–23°) are commercially available.

A second type of switching device employs the principle of total internal reflection (TIR) and is shown schematically in FIGS. 3 and 4. This device geometry was first suggested by Soref, for use as a fiber optic switch, and utilized a nematic liquid crystal as the active element. See R. A. Soref, "Low Cross-Talk 2×2 Optical Switch", Optics Letters, Vol 6 (1981), incorporated herein by reference. The device exhibits very high contrast ratios (<1000:1), but suffers from the same response time limitations as the previously described nematic devices.

The response time limitation in the above devices can be overcome by replacing the nematic material with a ferroelectric smectic liquid crystal; this has been demonstrated both by the applicant herein and also by Meadows et al. See M. R. Meadows, M. A. Handschy, and N. A. Clark, "Electro-optic Switching using Total Internal Reflection by a Ferroelectric Liquid Crystal", Appl Phys. Lett. 54 (15), 10 Apr. 1989, incorporated herein by reference. The ferroelectric TIR device is shown in FIGS. 5 and 6. An applied DC voltage rotates the molecules through a 90° angle, which changes the perceived refractive index from $n_o$ to $n_e$ and defeats the TIR effect as indicated in FIGS. 3 and 4. For a ferroelectric liquid crystal material to be useful in such a device, it must therefore possess a value of the molecular tilt angle $\theta$ of approximately 45°, since the molecule rotates through an angle approximately equal equal to $2\theta$ upon application of a DC field to the cell. This requirement for a large molecular tilt angle eliminates all but a few of the commercially available mixtures from consideration for use in TIR devices.

The prior art has suggested certain FLC compounds; see U.S. Pat. No. 4,892,676 to Sakurai it al and U.S. Pat. No. 4,880,561 to Tabohashi it al (1989) which compounds however, are nitorgen containing.

Accordingly, there is a need and market for improved FLC compounds and mixtures thereof that overcome the above prior art shortcomings.

There have now been discovered certain compounds which serve as highly suitable FLC materials with large molecular tilt angle, which compounds have further been formulated into several mixtures which are highly useful in FLC TIR switching devices.

SUMMARY

Broadly the present invention provides a high tilt angle FLC compound for TIR switching devices comprising compounds of the formula

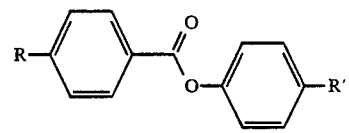

Where

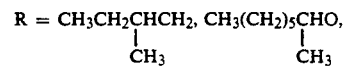

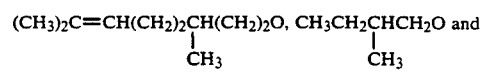

$R' = C_8H_{17}O, C_9H_{19}O, C_{10}H_{21}O,$

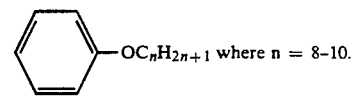

The above compounds include the following eight compounds listed below in Tables 1 and 2:

TABLE 1

| Structure | Phase transitions |
|---|---|
| CH₃(CH₂)₅CHO—⟨benzoate⟩—⟨biphenyl⟩—OC₈H₁₇, CH₃ branch<br>(R)-(−)-4′-n-octyloxybiphenyl-4-(1-methylheptyloxy)benzoate (OOBP1MeHepOB) | C →76.7→ S$_C^*$ →99.0→ Ch →122.0→ I |
| CH₃(CH₂)₅CHO—⟨benzoate⟩—⟨biphenyl⟩—OC₁₀H₂₁, CH₃ branch<br>(R)-(−)-4′-n-decyloxybiphenyl-4-(1-methylheptyloxy)benzoate (DOBP1MeHepOB) | C →65.6→ S$_C^*$ →103.4→ Ch →108.7→ I |
| (CH₃)₂C=CH(CH₂)₂CH(CH₂)₂O—⟨benzoate⟩—⟨biphenyl⟩—OC₈H₁₇, CH₃ branch<br>(R)-(+)-4′-n-octyloxybiphenyl-4-(3,7-dimethyloctenyloxy)benzoate (OOBPCit OB) | C →107.3→ S$_C^*$ →118.2→ Ch →142.0→ I |
| (CH₃)₂C=CH(CH₂)₂CH(CH₂)₂O—⟨benzoate⟩—⟨biphenyl⟩—OC₁₀H₂₁, CH₃ branch<br>(R)-(+)-4′-n-decyloxybiphenyl-4-(3,7-dimethyloctenyloxy)benzoate (DOBPCit OB) | C →99.3→ S$_C^*$ →115.4→ Ch →132.0→ I |
| CH₃CH₂CHCH₂—⟨benzoate⟩—⟨biphenyl⟩—OC₁₀H₂₁, CH₃ branch<br>(+)-4′-n-decyloxybiphenyl-4-(2-methylbutyl)benzoate (DOBP2MeBuB) (Compound 16) | C →51.2→ S$_C^*$ →129→ Ch →148→ I |

TABLE 2

| Structure | Phase transitions |
|---|---|
| CH₃CH₂CHCH₂O—⟨benzoate⟩—⟨phenyl⟩—OC₈H₁₇, CH₃ branch<br>(S)-(+)-4′-n-octyloxyphenyl-4-(2-methylbutoxy)benzoate (OOP2MeBuOB) | C →61.2→ I, I →48.7→ S$_C^*$, S$_C^*$ →44→ C |
| CH₃CH₂CHCH₂O—⟨benzoate⟩—⟨phenyl⟩—OC₉H₁₉, CH₃ branch<br>(S)-(+)-4′-n-nonyloxyphenyl-4-(2-methylbutoxy)benzoate (NOP2MeBuOB) | C →53.9→ I, I →45.2→ S$_C^*$, S$_C^*$ →38.2→ C |
| CH₃CH₂CHCH₂O—⟨benzoate⟩—⟨phenyl⟩—OC₁₀H₂₁, CH₃ branch<br>(S)-(+)-4′-n-decyloxyphenyl-4-(2-methylbutoxy)benzoate (DOP2MeBuOB) | C →48.9→ I, I →42.7→ S$_C^*$, S$_C^*$ →36→ C |

BRIEF DESCRIPTION OF THE DRAWINGS

The invention will become more apparent from the following detailed specification and drawings in which.

DESCRIPTION OF PREFERRED EMBODIMENTS

Figure 1:
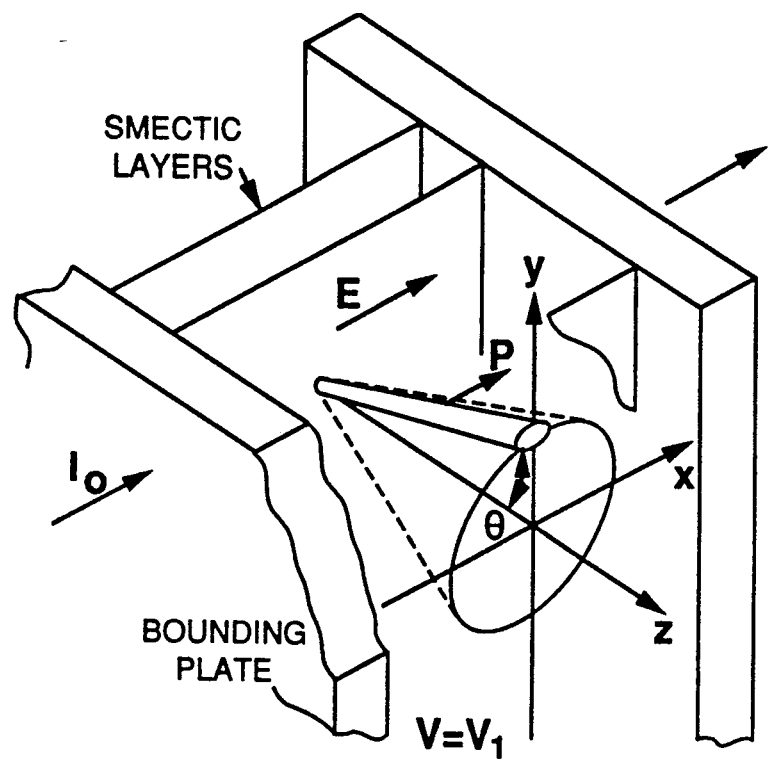
FIGS. 1 and 2 are schematic diagrams in perspective of a surface stabilized FLC cell of the prior art.
Figure 2:
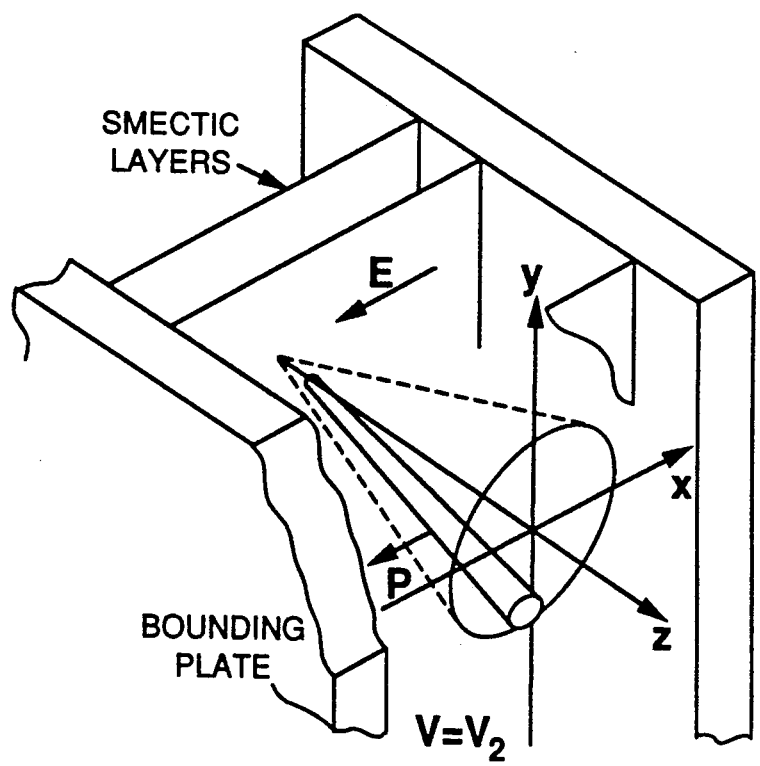
Figure 3:
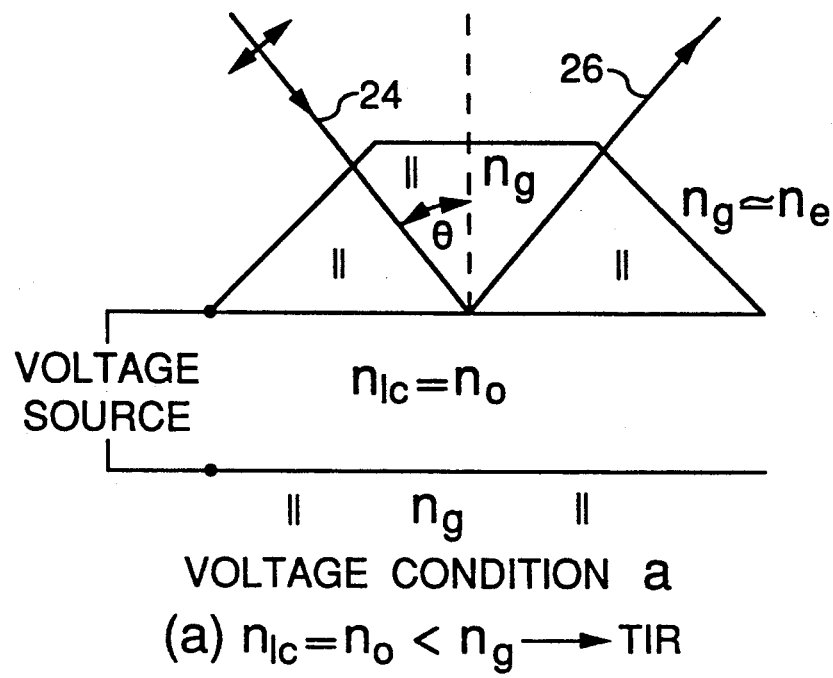
FIGS. 3 and 4 are schematic diagrams of a TIR beam deflector of the prior art and FIGS. 5 and 6 are schematic elevation views of a two position bi-stable TIR beam deflector of the prior art.
Figure 5:
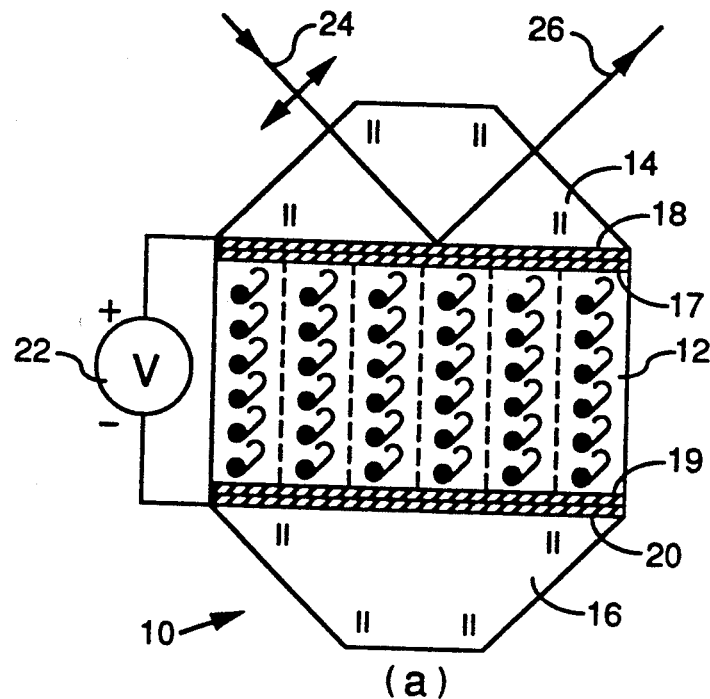
Figure 6:
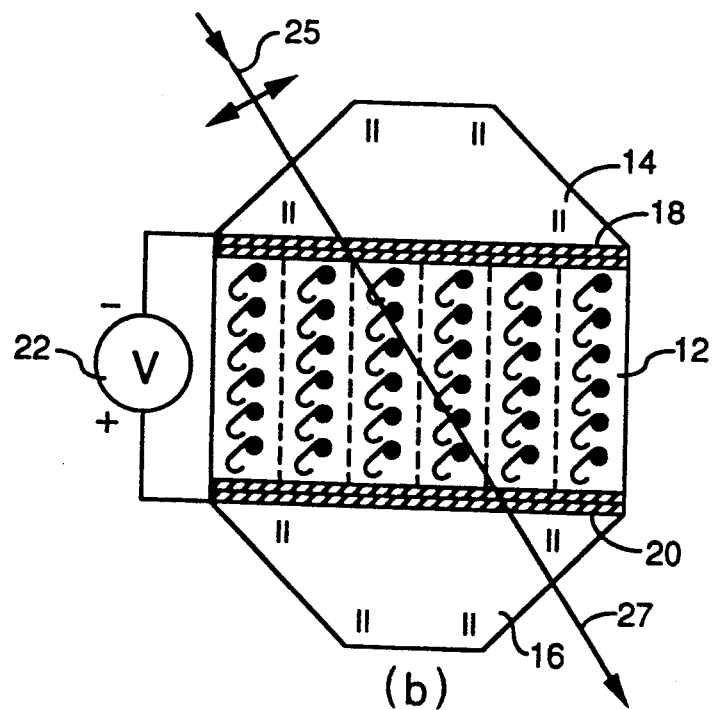

Referring now in more detail to the drawings, the prior art TIR switch 10 is made of an FLC mixture layer of some of the above compounds (of the invention) in the form of a sheet or film, between a pair of glass prisms 14 and 16, whose surfaces are coated with alignment layers 17 and 19 surmounted by transparent electrodes 18 and 20 as shown in FIGS. 5 and 6. The FLC mixture is made and positioned between the prisms 14 and 16, such that the long (optic) axis of most of the molecules of such mixture are aligned with the incoming (polarized) light beam. The other optic axis of the FLC layer 12 is also in the plane of such layer but is rotated by the angle $\theta$. At this point the FLC layer 12 has an index of refraction of $n_o$ which is less than the index of refraction of the glass prism 14 and the incoming light beam 24 is reflected by such glass prism, as reflected light beam 26, as shown in FIGS. 3 and 5.

Figure 4:
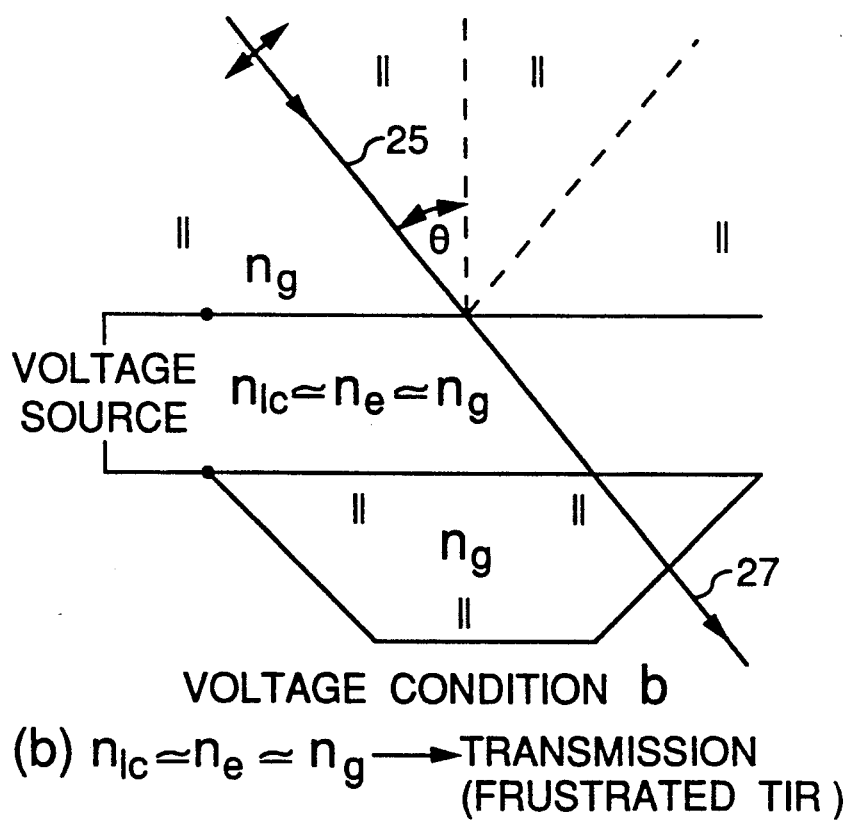

The DC voltage source 22 is turned on which rotates the FLC mixture molecules about 90° as shown in FIG. 6. Now the index of refraction of the FLC layer is converted from $n_o$ to $n_e$ which is about equal to the index of refraction of the prism, the TIR effect of such switch is overcome and the incoming light beam 25, instead of being reflected, passes through FLC beam deflector or switch and exits as beam 27, as shown in FIGS. 4 and 6.

Thus by reversing polarity of the voltage source 22 of the beam deflector 10, shown in FIGS. 3, 4, 5 and 6, incoming (polarized) light beams are reflected or transmitted in any desired pattern and frequency. These FLC beam deflectors or switches are suitable for switching polarized light eg. polarized laser beams.

As noted above, the switches of 5 and 6 are prior art while the FLC layers therein which include mixtures of the above compounds (of tilt angle $\theta$ of eg. 38° to 45°) that are the subject of the present invention.

Thus, employing the above compounds of the present invention, two formulation approaches were used; a) a single mixture approach in which six to eight compounds are combined directly to produce a mixture without regard for their (optical) helical twist sense and b) a composite mixture approach, in which two separate mixtures of opposite (optical) twist sense were separately formulated and blended together.

Examples of the single mixture approach are given below in Table 3.

TABLE 3

| Mixtures Formulated by the Single Mixture Approach | | | |
|---|---|---|---|
| KE-19 | | KE-23 | |
| OOP2MeBuOB | 7.4% | OOP2MeBuOB | 5.3% |
| NOP2MeBuOB | 10.0% | NOP2MeBuOB | 9.7% |
| DOP2MeBuOB | 15.0% | DOP2MBuOB | 9.6% |
| DOBP2MeBuB | 13.2% | DOBP2MeBuB | 36.6% |
| DOBP1MeHepOB | 26.5% | OOBP1MeHepOB | 14.8% |
| DOBPCitOB | 12.0% | DOBP1MeHepOB | 21.4% |
| OOBPCitOB | 15.8% | OOBPCitOB | 2.7% |
| KE-28 | | | |
| OOP2MeBuOB | 7.1% | | |
| NOP2MeBuOB | 12.4% | | |
| DOP2MeBuOB | 13.6% | | |
| DOBP2MeBuB | 39.8% | | |
| OOBP1MeHepOB | 16.3% | | |
| OOBPCitOB | 3.0% | | |
| DOP1MeHepOT | 5.2% | | |

Three mixtures of compounds of the invention are given in Table 3 above, KE-19, KE-23 and KE-28. The percentages given in Table 3 and in the Tables to follow as "%" are to be read as "wt.%" and each listed compound has a range of ±3.0 wt. % in its respective mixture, within the scope of the present invention. For example, the first compound of KE-19 which is stated to be present in the mixture in the amount of 7.4% is to be read as having a range of 4.4 to 10.4 wt. % therein per the scope of the present invention; the other percentages listed in this and subsequent Tables to be similarly read.

Examples of the composite mixture approach are given below in Table 4.

TABLE 4

| Composite Mixture Approach Left- and right-handed mixtures used for blending | | | | | |
|---|---|---|---|---|---|
| Mixture RH | | Mixture RH-2 | | Mixture LH | |
| OOP2MeBuOB | 10.3% | OOP2MeBuOB | 12.4% | OOBP1MeHepOB | 26.5% |
| NOP2MeBuOB | 17.3% | NOP2MeBuOB | 20.0% | DOBP1MeHepOB | 37.4% |
| DOP2MeBuOB | 19.3% | DOP2MeBuOB | 20.4% | OOP1MeHepOT | 22.5% |
| DOBP2MeBuB | 46.0% | DOBP2MeBuB | 47.1% | DOP1MeHepOT | 3.6% |
| OOBPCitOB | 4.1% | | | | |
| $S_B$-$S_C^*$: 26.0 | | $S_I$-$S_C^*$: <25 | | $S_I$-$S_C^*$: <25 | |
| $S_C^*$-Ch: 54.6 | | $S_C^*$-Ch: 54.6 | | $S_C^*$-Ch: 56.9 | |
| Ch-I: 100.7 | | Ch-I: 94.6 | | Ch-I: 80.0 | |

Table 4 above lists two right-handed mixtures (in the optical sense) mixture RH and mixture RH-2. Such Table also lists one left-handed mixture, mixture LH as shown.

As further shown mixture RH of Table 4 has a ferroelectric smectic C range of between 26° to 54.6° C. a range where the FLC molecules can reorient under application of a DC electric field, through an angle which is approximately equal to $2\theta$. This is known as the $S_c^*$ range, which, as shown in Table 1 above, are higher for individual compounds than for the mixtures thereof shown, eg. in Tables 3 and 4 and in some cases lower than the individual compounds shown in Table 2. Blending these compounds lowers the operating temperature range thereof for more convenient employment thereof, eg. in optical switching devices.

Thus the invention provides novel compounds which answer a requirement for a large molecular tilt angle $\theta$, eg. of about 45°.

The invention further provides mixtures of the above compounds for more effective use thereof for the following purposes:

1) to lower the $S_c^*$ temperature to a desired range, eg. from 19° to 30° C.;
2) to lengthen the effective helical pitch of the resultant mixture of the compounds of the invention so that a) the molecules will more readily align with the polarization of the incoming beam, b) that the resultant mixture will retain a molecular tilt angle of between 38 to 45 degrees and c) that the molecules of such mixture will, upon application of a DC voltage field, rotate together through an angle of $2\theta$ or about 90°.
3) the mixture is desirably formulated to have a switching voltage of eg. between 20 to 50 volts.

Note that in the compounds of Table 2, the $S_c^*$ value is below the crystallization temperature thereof. With such liquid crystal compounds, which are termed monotropic, it is more difficult to produce and maintain a stable mixture with an $S_c^*$ operating range near room temperature (about 20° C.). However, these compounds, when mixed with the compounds of Table 1, termed enantiotropic, form a stable mixture of reduced $S_c^*$ operating temperature range.

Returning to the composite mixtures of Table 4, blending an LH mixture with an RH mixture is a way to lengthen the effective helical pitch thereof for the advantages noted above.

A preferred mixture is that shown in Table 5 below, having a blend of 15 wt. % LH in RH-2.

TABLE 5

Composite Mixtures Formulated
. Trial mixtures formulated ranging from 10–30% LH in RH-2
. Optimum concentration range between 10–20% LH in RH-2

| 15% LH in RH-2 | |
|---|---|
| OOP2MeBuOB | 10.5% |
| NOP2MeBuOB | 17.0% |
| DOP2MeBuOB | 17.3% |
| DOBP2MeBuB | 40.0% |
| OOBP1MeHepOB | 4.0% |
| DOBP1MeHepOB | 5.6% |
| OOP1MeHepOT | 3.4% |
| DOP1MeHepOT | 2.0% |

$S_1$-$S_C^*$: <25
$S_C^*$-Ch: 50.2
Ch-I: 94.8

TILT ANGLE = 42°

The above mixture exhibits an operating temperature range or $S_c^*$ range, of between 25° to 50.2° C. and a tilt angle $\theta$ of 42°.

Further the addition of 5% by weight of a nematic liquid crystal (PPMeOB/PPPOB) to 15% LH in RH-2 of Table 5, has resulted in switching devices with improved alignment and reduced response time at the cost of a slight reduction of the tilt angle to 38°.

The various mixtures discussed above displayed operating temperature ranges from slightly less than 25° C. up to 60° C., depending upon the composition thereof.

The smectic FLC compounds and mixtures thereof of the present invention provide for TIR switches that exhibit high contrast ratios ( 1,000:1). They further provide in such switch, 2-position bistable beam deflection, provided that appropriate substrate surface treatments and cell gap spacings are employed. Such conditions are described in the in the prior art, eg. in the Clark and Lagerwall Article cited above. That is, if the electric field of the TIR switches shut off, the smectic FLC will hold the molecular tilt angle existing at that time without requiring an applied electric field to hold such pattern, unlike their nematic LC predecessors.

The ferroelectric smectic liquid crystal compounds of the invention and mixtures formulated from them, also of the invention, are useful for a high speed modulation or switching of optical radiation. Such uses include, eg. high speed light valves, photocopy heads, laser beam deflectors and optical power limiters.

What is claimed is:

1. High tilt angle FLC compounds for TIR switching devices comprising, compounds of the formula:

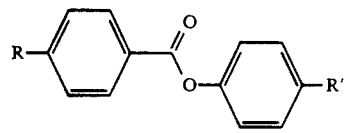

Where $R = (CH_3)_2C=CH(CH_2)_2\underset{\underset{CH_3}{|}}{C}H(CH_2)_2O$ and

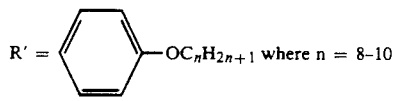  where $n = 8-10$

* * * * *